US010364203B2

United States Patent
Crockatt et al.

(10) Patent No.: US 10,364,203 B2
(45) Date of Patent: Jul. 30, 2019

(54) METHOD FOR PREPARING PHENOLICS USING A CATALYST

(71) Applicant: Nederlandse Organisatie voor toegepast-natuurwetenschappelijk onderzoek TNO, 's-Gravenhage (NL)

(72) Inventors: Marc Crockatt, 's-Gravenhage (NL); Paul Mathijs Könst, 's-Gravenhage (NL); Jan Harm Urbanus, 's-Gravenhage (NL); Dennis Johannes Maria Snelders, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 0 days.

(21) Appl. No.: 16/064,871

(22) PCT Filed: Dec. 22, 2016

(86) PCT No.: PCT/NL2016/050912
§ 371 (c)(1),
(2) Date: Jun. 21, 2018

(87) PCT Pub. No.: WO2017/111595
PCT Pub. Date: Jun. 29, 2017

(65) Prior Publication Data
US 2019/0002379 A1    Jan. 3, 2019

(30) Foreign Application Priority Data
Dec. 22, 2015   (EP) ..................... 15202128

(51) Int. Cl.
*C07C 37/14*   (2006.01)
*C07C 67/347*   (2006.01)
*B01J 21/04*   (2006.01)
*B01J 21/08*   (2006.01)
*B01J 21/12*   (2006.01)
*B01J 31/22*   (2006.01)
*C07C 39/06*   (2006.01)

(52) U.S. Cl.
CPC ............. *C07C 37/14* (2013.01); *B01J 21/04* (2013.01); *B01J 21/08* (2013.01); *B01J 21/12* (2013.01); *B01J 31/2226* (2013.01); *C07C 67/347* (2013.01); *B01J 2531/36* (2013.01); *B01J 2540/225* (2013.01); *C07C 39/06* (2013.01)

(58) Field of Classification Search
None
See application file for complete search history.

(56) References Cited

FOREIGN PATENT DOCUMENTS

WO    WO 2016/114668 A1    7/2016

OTHER PUBLICATIONS

Moreno et al., An Efficient One-Pot Synthesis of Phenol Derivatives by Ring Opening and Rearrangement of Diels-Alder Cycloadducts and Substituted Furans Using Heterogeneous Catalysis and Microwave Irradiation, Synlett, No. 7, pp. 1259-1263, 2004.
Shinohara et al., Ircl3 or FeCl3-catalyzed convenient synthesis of 3-hydroxyphthalates, Tetrahedron Letters, 52, 6238-6241, 2011.

*Primary Examiner* — Medhanit W Bahta
(74) *Attorney, Agent, or Firm* — Arent Fox LLP

(57) ABSTRACT

The invention is directed to a method for preparing a phenolic compound comprising reacting a furanic compound with a dienophile in the presence of a catalyst comprising yttrium.

18 Claims, No Drawings

METHOD FOR PREPARING PHENOLICS USING A CATALYST

The invention relates to the production of phenolic compounds from furanic compounds. In particular, the invention is related to the production of phenolic compounds from furanic compounds using a catalyst.

Phenolic compounds and in particular phenol are important bulk chemicals and are of great interest for a wide variety of applications. It is preferable to produce phenols from bio-renewable compounds, i.e. compounds that are based on biomass and do not have a petrochemical origin, as this offers a long term sustainable solution for production.

Currently, production of benzene-derived aromatics (e.g. benzene, toluene, xylene and phenols) from biomass is not commercialized, although several technologies are under development. A preferred method is to unravel and treat components from biomass separately, allowing for separated conversion paths. By such a method, furanic compounds (e.g. furfural, 2-methylfuran, furfuryl alcohol, furan) are currently produced from biomass on a relatively large scale. An efficient conversion of furanic compounds into phenols is therefore highly desirable.

The reaction of furanic compounds into phenolic compounds generally involves cycloaddition, such as a Diels-Alder reaction. Lewis acids are known as catalysts for Diels-Alder reactions in general. Common catalysts include aluminum, zinc and titanium halides. These catalysts were found to give unsatisfying results for the reaction of furanic compounds into phenolic compounds.

Moreno et al., *Synlett*, 7 (2004) 1259-1263 disclose the use of silica-supported Lewis acids, such as silica supported alumina, zinc and titania, as catalysts for the production of polysubstituted phenols from furanic compounds. For the reaction of 2-ethylfuran with methyl propiolate, a 56% yield was obtained, however a 6:1 molar ratio of furanic compound to dienophile was required. Accordingly, this process is not commercially viable.

Brimble et al., *Organic & Biomolecular Chemistry* 6 (2008) 4261-4270 disclose the reaction of 2-methylfuran with methyl propiolate using aluminum(III) chloride ($AlCl_3$) and dichloromethane at 0° C. giving 42% yield at 1 h.

WO 2008071736; WO2009150118; WO2009150119; WO 2009072581 report the reaction of 2-methylfuran with ethyl-2-propiolate using $AlCl_3$ and dichloromethane giving 32% yield.

Accordingly, there is a need for improved methods for the catalyzed reaction of a furanic compound with a dienophile to obtain a phenolic compound.

Surprisingly, the present inventors have found that this can be achieved by reacting the furanic compound with the dienophile in the presence of a catalyst comprising yttrium.

The yttrium is typically present in an oxidized state such as yttrium(III). The catalyst preferably further comprises at least one ligand. Particularly good results have been achieved by using sulfonate ligands.

The sulfonate ligand typically has a structure that can be represented by $—SO_3R$, wherein one of the oxygens typically coordinates to the catalyst. The sulfonate ligand typically comprises an alkyl or aryl group, for instance methyl, phenyl, p-toluene and the like. The alkyl or aryl group may be substituted with e.g. one or more heteroatoms, linear or branched alkyls and the like. The alkyl or aryl group may be substituted with one or more halides, nitro, carboxylic acid and the like, such that the alkyl or group is an electron withdrawing group.

In a preferred embodiment, the sulfonate ligand comprises an electron-withdrawing (e.g. R is an electron-withdrawing group). An example of an electron withdrawing group is 4-nitrophenyl.

In a further preferred embodiment, the electron-withdrawing group is a halogenated group comprising at least one halogen atom, more preferably a perhalogenated group, even more preferably a perfluoroalkyl, most preferably a trifluoromethyl group.

With perhalogenated is meant herein that all carbon atoms in the compound are only bound to another carbon, to a halogen atom and/or to a heteroatom. As such, the perhalogenated group does not comprise carbon-hydrogen bonds. Examples of preferred perhalogated groups are trichloromethane and pentafluorophenyl but also sulfonated tetrafluoroethylene based fluoropolymer-copolymers (e.g. those known under the tradename Nafion™). Accordingly, it is preferable that the catalyst of the present invention comprises yttrium(III) triflate.

The catalyst of the present invention can be a homogeneous catalyst or a heterogeneous catalyst. In case the catalyst is a heterogeneous catalyst, the catalyst is applied on a solid support, which can for instance be a polymeric support, silica, alumina or silica-alumina, such as a zeolite. The advantage of applying the catalyst in a solid support is that this facilitates the recovery and/or recycling of the catalyst.

In a particular embodiment, the catalyst can for instance be applied to the solid support by ion exchange. For example, a resin comprising sulfonate groups can be used, such as crosslinked styrene divinylbenzene copolymers comprising sulfonic acid groups (e.g. those known under the tradename Amberlyst™ 15) or perfluorated polymers such as sulfonated tetrafluoroethylene based fluoropolymer-copolymers (e.g. those known under the tradename Nafion™). The solid support may thus comprise anionic groups, preferably sulfonate, carboxylate and/or phosphonate groups, which can for instance form coordinating bonds with the yttrium in the catalyst.

The catalyst is usually included in the reaction mixture in an amount of 0.0001 to 1 equivalent, based on the furanic compound.

In the present invention, the furanic compound is reacted with a dienophile to obtain a phenolic compound. Such a reaction proceeds typically according to the following general reaction scheme:

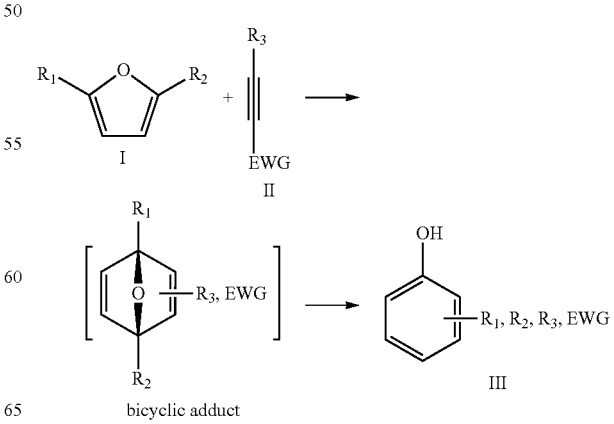

wherein the furanic compound can be represented by formula I, the dienophile can be represented by formula II and the phenolic compound can be represented by formula III.

Without wishing to be bound by theory, the inventors believe that the phenolic compound is formed via a bicyclic adduct that is formed as an intermediate.

Typically, the bicyclic adduct undergoes a ring-opening in situ. However, in a particular embodiment of the present invention, the phenolic compound is obtained by ex-situ ring-opening of a bicyclic adduct that is obtained after reacting the furanic compound with the dienophile.

In the present invention, the furanic compound may be considered as a diene. A reaction between a diene and a dienophile is known in the field as a Diels-Alder reaction. As such, for the present invention the reaction of the furanic compound with the dienophile may be referred to as the Diels-Alder reaction. However, it will be appreciated that the present invention is directed to any reaction of the furanic compound with a dienophile, independently of the specific reaction pathway of mechanism involved. For instance, although the Diels-Alder reaction is a concerted reaction, viz. a single-step reaction without any intermediate, a non-concerted reaction such as e.g. a Friedel-Craft-type pathway is also within the scope of the present invention.

In the present invention, the furanic compound may be provided as such, or as a precursor thereof. Such precursors are generally well known in the field. For instance, hexane-2,5-dione can be in situ converted into furanics.

In the present invention, a furanic compound is for example a compound based on formula

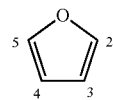

and is typically substituted on the 2, 3, 4 and/or 5 position by one or more alkyl chains, heteroatoms and/or halogens. Said alkyl chains are typically $C_1$-$C_8$-alkyls and can be linear or branched and can be optionally substituted by halogens and/or heteroatoms. The furanic compound may be bound to a solid support so that purification after a reaction may be facilitated. In a particular embodiment of the present invention, the furanic compound is substituted on the 2 and/or 5 position.

The furanic compound in accordance with the present invention is preferably a compound according to formula I

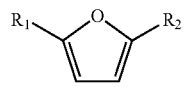

wherein $R_1$ and $R_2$ are independently selected from the group consisting of H, linear or branched $C_1$-$C_8$-alkyl, F, Cl, Br, I, —$CH_2F$, —$CH_2Cl$, —$CH_2Br$, —$CH_2I$, —CN, —$NO_2$, —CHO, —$CO_2H$ and esters thereof, —$CH_2NH_2$ and secondary, tertiary and quaternary amines or amides thereof and —$CH_2OH$ and esters or ethers thereof, optionally bound to a solid support.

The furanic compounds according to formula I can be derived from biomass, for instance from $C_5$ and $C_6$ carbohydrates. It is preferred that the furanic compound is a relatively simple furanic compound (i.e. inter alia having a low molecular weight) to reduce the necessity of further reactions to produce an industrially relevant phenolic product. It is therefore particularly preferred that the furanic compound is a compound according to formula I wherein $R_1$ and $R_2$ are independently a hydrogen, linear or branched $C_1$-$C_4$-alkyl, —CHO, —$CH_2OH$ or an ester or a ether thereof, or —$CO_2H$ and esters thereof. It is more preferred that $R_1$ and $R_2$ are independently a hydrogen, methyl, ethyl, —CHO, —$CH_2OH$ and ester or ethers thereof, or —$CO_2H$ and esters thereof, more preferably wherein $R_1$ is hydrogen and $R_2$ is selected from the group consisting of hydrogen, methyl, —CHO, —$CH_2OH$ and esters and ethers thereof, and —$CO_2H$ and esters thereof. Most preferred is that $R_1$ is hydrogen and $R_2$ is selected from the group consisting of hydrogen, methyl and —$CH_2OH$ and esters and ethers thereof.

A particular advantage of the specific embodiments as described in the previous paragraph wherein $R_1$ is hydrogen and $R_2$ is methyl, —CHO, —$CH_2OH$ or —$CO_2H$ and esters thereof, is that the furanic compound can be derived from a $C_5$ carbohydrate with full retention of all carbon atoms of the $C_5$ carbohydrate and thus with a good atom efficiency. These embodiments are thus particularly environmentally benign and cost efficient.

In the present invention, the dienophile generally comprises a triple bond.

The inventors found that for the present invention preferably acetylene, optionally substituted with one or more linear or branched $C_1$-$C_8$-alkyl groups or an acetylene derivative according to the following formula II is used as the dienophile.

wherein EWG is an electron withdrawing group and $R_3$=H, linear or branched $C_1$-$C_8$-alkyl, or EWG. More preferably EWG=—CN, —$NO_2$, —$CO_2X$, —C(O)NX, —C(=NY)X, $CF_3$, $CCl_3$, $CBr_3$, $CI_3$, —$SO_2$, —$SO_3X$, —COH, —COX, —COF, —COCl, —COBr, —COI, wherein X and Y are independently H, or linear or branched $C_1$-$C_8$-alkyl, optionally substituted with halogens and optionally polymer-supported.

Acetylene derivatives according to formula II are easily obtainable from acetylene by a reaction of acetylene with e.g. $CO_2$ followed by further basic manipulations. These acetylene derivatives according to formula II are typically commercially available.

The dienophile according to formula II reacts particularly well with the furanic compound of the present invention. The electron withdrawing group EWG results in an electron poor triple bond which reacts more rapidly with an electron rich furanic.

Reacting the furanic compound with the dienophile can be carried out at a temperature ranging from −60-350° C., preferably −20-250° C., more preferably 20-180° C. The precise temperature depends on the specific furanic compound and dienophile used.

Reacting the furanic compound with the dienophile can be carried out at a pressure ranging from 0-200 bar, preferably 1-50 bar.

Reacting the furanic compound with the dienophile can be carried out in a solvent. Solvents selected from the group consisting of water, alcohols, esters, ketones, aliphatic hydrocarbons, aromatic hydrocarbons, organic acids, ethers, diprotic apolar solvents, halogenated solvents, nitrated solvents, ionic liquids, organic bases and combinations thereof can for instance be used. Particularly good results are obtained when the reaction is carried out in an apolar, aprotic and/or non-coordinating solvent, such as a $C_4$-$C_{12}$ hydrocarbon or ethers and esters, for example toluene, heptane or mesitylene. These type of solvents are thus preferred.

Preferred concentrations are those between 0.1-3 M, more preferably about 2 M.

Typical phenolic compounds that result from reacting the furanic compound with the dienophile comprise a phenolic moiety:

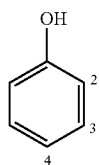

that is typically substituted on the 2, 3 and 4 position with one or more alkyl chains, heteroatoms and/or halogens. Said alkyl chains are typically $C_1$-$C_8$-alkyls and can be linear or branched and can be optionally substituted by halogens and/or heteroatoms. In particular, the phenolic compound is preferably a compound according to formula III

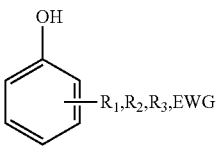

III wherein EWG, $R_1$, $R_2$ and $R_3$ are as defined herein above.

The reaction may yield a variety of regio-isomers as indicated with formula III. In particular one or more of the regio-isomers as schematically represented with formulae IIIa-IIIh below can be obtained.

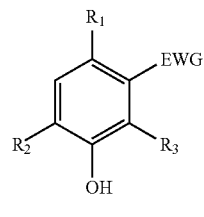

IIIa

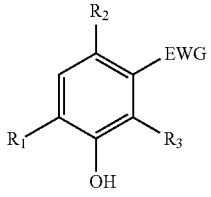

IIIb

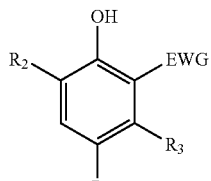

IIIc

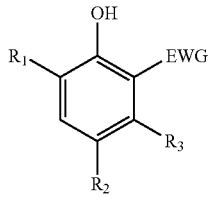

IIId

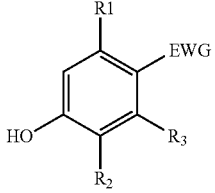

IIIe

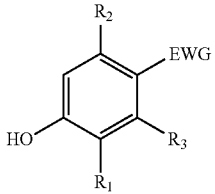

IIIf

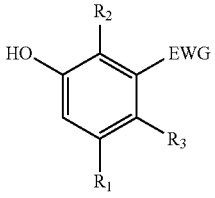

IIIg

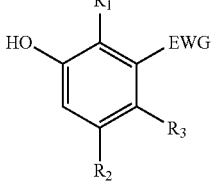

IIIh

In a particular embodiment of the present invention, furanic compounds derivable from $C_4$-sugars and/or $C_4$-sugar alcohols are reacted in the Diels-Alder reaction. Typically, $C_4$-sugars are converted into furan, i.e. the compound according formula I wherein $R_1$=$R_2$=H. Reactions with such furanics generally yield products according formula III (or one or more of IIIa to IIIh), wherein $R_1$=$R_2$=H.

In another particular embodiment of the present invention, furanics derivable from $C_5$-sugars are reacted in the Diels-Alder reaction with dienophiles. Typically, $C_5$-sugars are converted into mono-substituted furanics, e.g. compounds according formula I wherein $R_1$=H and $R_2$ may be selected from the group consisting of linear or branched $C_1$-$C_8$-alkyl, F, Cl, Br, I, —$CH_2F$, —$CH_2Cl$, —$CH_2Br$, —CH$_2$I, —CN, —NO$_2$, —CHO, —CO$_2$H and esters thereof, —CH$_2$NH$_2$ and secondary, tertiary and quaternary amines or amides thereof and —CH$_2$OH and esters or ethers thereof, optionally bound to a solid support. Reactions with such furanics generally yield products according formula III (or one or more of IIIa to IIIh), wherein R$_1$=H.

In yet another particular embodiment of the present invention, furanics derivable from C$_6$-sugars are reacted in the Diels-Alder reaction with dienophiles. Usually C$_6$-sugars are converted into bis-substituted furanics, e.g. compounds according formula I wherein R$_1$ and R$_2$ are not hydrogen and may be independently selected from the group consisting of linear or branched C$_1$-C$_8$-alkyl, F, Cl, Br, I, —CH$_2$F, —CH$_2$Cl, —CH$_2$Br, —CH$_2$I, —CN, —NO$_2$, —CHO, —CO$_2$H and esters thereof, —CH$_2$NH$_2$ and secondary, tertiary and quaternary amines or amides thereof and —CH$_2$OH and esters or ethers thereof, optionally bound to a solid support.

Herein, the term C$_6$-sugar refers to carbohydrate monomers comprising six carbon atoms and the term C$_5$-sugar refers to carbohydrate monomers comprising five carbon atoms. For instance, carbohydrate polymers such as starch, cellulose and inulin comprise C$_6$-sugar units such as glucose and fructose. The carbohydrate polymers hemicellulose and pectin comprise for instance C$_5$-sugar units such as xylose and arabinose and C$_6$-sugar units such as rhamnose and galactose. Sucrose is a dimer of the C$_6$-sugar units glucose and fructose.

Alternatively to the direct conversion of C$_4$, C$_5$ or C$_6$-sugars and/or sugar alcohols into furanics, furanic compounds can also be obtained through the removal or addition of side-groups of furanics. Furan, for instance, can be obtained from furfural through decarbonylation. 2,5-Furandicarboxylic acid can be obtained from 2-furoic acid by deprotonation of carbon 5, followed by addition of carbon dioxide. In addition, furan can also be obtained from 1,3-butadiene through oxidation with a metal catalyst and oxygen gas. The phenolic compound resulting from the Diels-Alder reaction is optionally further reacted in one or more reactions selected from the group consisting of hydrolysis, reduction, oxidation, decarboxylation, decarbonylation, nucleophilic addition, olefination, rearrangement and combinations thereof. In a particular embodiment of the present invention wherein the phenolic compound is a compound according to formula III, this reaction generally involves conversion of R$_1$, R$_2$, R$_3$ or EWG or any combination thereof.

It is particularly preferable that the phenolic compound is further reacted to a final phenol product such as a bulk phenol, i.e. a phenol produced at bulk scale.

A preferred final phenol product is accordingly selected from the group consisting of phenol, o-alkylphenol, m-alkylphenol, p-alkylphenol, (e.g. cresols) o-hydroxybenzoic acid, m-hydroxybenzoic acid, p-hydroxybenzoic acid, 2,6-dialkylphenol, 2,5-dialkylphenol, 2,4-dialkylphenol, 2,3-dialkylphenol, 3,4-dialkylphenol, 3,5-dialkylphenol, (e.g. xylenols), 2,3,4-trialkylphenol, 2,3,5-trialkylphenol, 2,3,6-trialkylphenol, 2,4,5-trialkylphenol, 2,4,6-trialkylphenol, 3,4,5-trialkylphenol, o-nitrophenol, m-nitrophenol, p-nitrophenol, o-cyanophenol, m-cyanophenol, p-cyanophenol, catechol, resorcinol, hydroquione, o-halophenol, m-halophenol, p-halophenol, o-aminophenol, m-aminophenol. p-aminophenol, o-hydroxystryrene, m-hydroxystyrene, p-hydroxystyrene, o-hydroxybenzyl alcohol, m-hydroxybenzyl alcohol, p-hydroxybenzyl alcohol, o-hydroxybenzyl amine, m-hydroxybenzyl amine, p-hydroxybenzyl amine, o-hydroxyacetophenone, m-hydroxyacetophenone, p-hydroxyacetophenone, o-hydroxybenzaldehyde, m-hydroxybenzaldehyde, p-hydroxybenzaldehyde, o-hydroxybenzamide, m-hydroxybenzamide, p-hydroxybenzamide and combinations thereof.

According to the present invention, phenol can thus be obtained by reacting furan (i.e. compound of formula I, wherein R$_1$=R$_2$=H) with a propynoate (i.e. compound of formula II, wherein EWG=CO$_2$X and R$_3$=H), thereby obtaining a mixture of the phenolic compounds of formula III, wherein R$_1$=R$_2$=R$_3$=H, EWG=CO$_2$X. This specific phenolic compound is then subsequently reacted in a decarboxylation reaction or in a hydrolysis and a subsequent decarboxylation reaction.

For the purpose of clarity and a concise description, features are described herein as part of the same or separate embodiments. However, it will be appreciated that the scope of the invention may include embodiments having combinations of all or some of the features described.

The invention is further illustrated by the following examples.

EXAMPLES

Example 1

A catalyst (about 0.09 mmol, 0.1 equivalent) was weighed into a reactor and dissolved in toluene (0.5 mL). Methyl propiolate (MP) (80.1 µL, 1 equivalent) was added to the mixture, then 2-methylfuran (2-MF) (85.2 µL, 1.05 equivalent) was added. The reaction mixture was stirred for 2 h at 140° C. The product (2-methyl-5-hydroxymethylbenzoate, MHMB) was obtained by evaporation, addition of dichloromethane, washing with water, drying and filtration. The yield was determined by HPLC.

Table 1 shows as comparative result that AlCl$_3$ and aluminium(III) trifluoromethanesulfonate (Al(OTf)$_3$) as catalyst provided a yield of 0-3%, except for THF which provided 19% yield (with 48% 2-MF remaining)

TABLE 1

Comparative examples

| Catalyst | Mol % catalyst | Solvent | T (° C.)/t | Yield |
|---|---|---|---|---|
| AlCl$_3$ | 12% | THF | 140/2 H | 19% |
| AlCl$_3$ | 8% | Toluene | RT/16 H | 2% |
| AlCl$_3$ | 12% | MeCN | 140/2 H | 0% |
| AlCl$_3$ | 17% | MeOH | 140/2 H | 0% |
| AlCl$_3$ | 17% | EtOAc | 140/2 H | 3% |
| Al(OTf)$_3$ | 9% | THF | 140/2 H | 2% |
| Al(OTf)$_3$ | 9% | Toluene | 140/2 H | 2% |
| Al(OTf)$_3$ | 11% | MeCN | 80/2 H | 1% |
| Al(OTf)$_3$ | 13% | MeOH | 80/2 H | 1% |
| Al(OTf)$_3$ | 14% | EtOAc | 80/2 H | 0% |

Surprisingly high yields were obtained with yttrium(III) trifluoromethanesulfonate (Y(OTf)$_3$) as catalyst, as shown in Table 2.

TABLE 2

| Catalyst | Eq. catalyst | Solvent | T (° C.)/t | Yield |
|---|---|---|---|---|
| Y(OTf)$_3$ | 6% | THF | 140/2 H | 34% |
| Y(OTf)$_3$ | 10% | Toluene | 140/2 H | 78% |
| Y(OTf)$_3$ | 9% | MeCN | 140/2 H | 46% |
| Y(OTf)$_3$ | 8% | MeOH | 140/2 H | 6% |
| Y(OTf)$_3$ | 73% | EtOAc | 140/2 H | 37% |

For Y(OTf)$_3$ as catalyst, a yield of 76% was obtained with heptane and a yield of 78% with mesitylene as solvent (using the same procedure).

Example 2

A supported catalyst was prepared by washing Amberlyst™ 15 resin in a column with methanol and water and a saturated Na$_2$SO$_4$ solution until the eluent in neutral, washing with water and drying to give the Na$^+$ exchanged resin. The resin (2 g) was contacted with the catalyst Y(OTf)$_3$ (2 mmol) and ethanol (5 mL) for 16 hours, then the solvent was filtered off, the resin washed thoroughly, and then dried. The reaction of 2-MF and MP was performed with this catalyst at 120° C. After about 45 hour the yield was about 30%.

Example 3

An experiment as in Example 1 was performed, but the 2-MF (1.05 eq.) was added continuously over 180 minutes to a solution of 2.86 mol/L MP in toluene, with Y(OTf)$_3$ (0.05 eq.) as catalyst, at 150° C., provided a 79% yield of MHMB.

Example 4

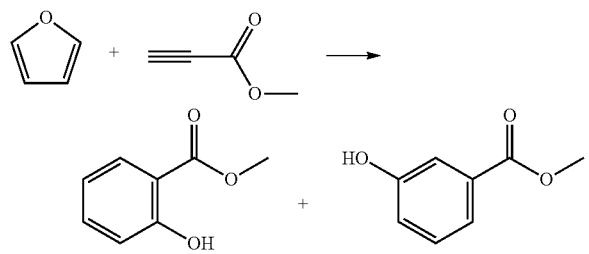

Yttrium triflate (0.11 mmol, 0.01 equivalent) was weighed into a reactor and dissolved in toluene (6.5 mL). Methyl propiolate (MP) (960 µL, 1 equivalent) was added to the mixture, then furan (809 µL, 1.1 equivalent) was added. The reaction mixture was heated to 140° C. and stirred for 6 h. The reaction mixture was cooled to room temperature then washed with saturated sodium bicarbonate solution, then water. The organics were dried over sodium sulfate, filtered and reduced to an oil. This was purified by column chromatography to methyl 2-hydroxybenzoate (27% yield) and methyl 2-hydroxybenzoate (31% yield).

Example 5

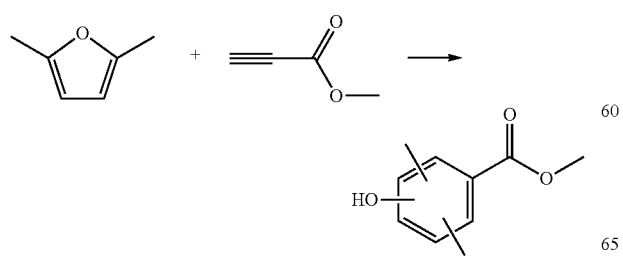

Yttrium triflate (0.11 mmol, 0.01 equivalent) was weighed into a reactor and dissolved in toluene (6.5 mL). Methyl propiolate (MP) (960 µL, 1 equivalent) was added to the mixture, then 2,5-dimethylfuran (1282 µL, 1.1 equivalent) was added. The reaction mixture was heated to 140° C. and stirred for 2 h. The reaction mixture was cooled to room temperature then washed with saturated sodium bicarbonate solution, then water. The organics were dried over sodium sulfate, filtered and reduced to an oil. This was purified by column chromatography to 4 separate regioisomers of the desired product (Combined yield=83%).

Example 6

A supported catalyst was prepared by washing Amberlyst™ 15 resin in a column with methanol and water and a saturated Na$_2$SO$_4$ solution until the eluent in neutral, washing with water and drying to give the Na$^+$ exchanged resin. The resin (2 g) was contacted with the catalyst Y(OTf)$_3$ (2 mmol) and ethanol (5 mL) for 16 hours, then the solvent was filtered off, the resin washed thoroughly, and then dried. The reaction of 2,5-dimethylfuran and methyl propiolate was performed at 120° C. using this catalyst. After 16 hours, reaction mixture was cooled to room temperature then filtered to remove the catalyst, and the filtrate was washed with water. The organics were dried over sodium sulfate, filtered and reduced to an oil. This was purified by column chromatography yield the same 4 products as were isolated in the reaction with the non-supported catalyst (Combined yield=77%).

The invention claimed is:

1. Method for preparing a phenolic compound comprising reacting a furanic compound with a dienophile in the presence of a catalyst comprising yttrium.

2. Method according to claim 1, wherein the catalyst further comprises a ligand.

3. Method according to claim 1, wherein the catalyst comprises yttrium(III) triflate.

4. Method according to claim 1, wherein the catalyst is applied on a solid support.

5. Method according to claim 1 wherein the furanic compound is a compound according to formula I

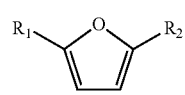

wherein R$_1$ and R$_2$ are independently selected from the group consisting of H, linear or branched C$_1$-C$_8$ alkyl, F, Cl, Br, I, —CH$_2$F, —CH$_2$Cl, —CH$_2$Br, —CH$_2$I, —CN, —NO$_2$, —CHO, —CO$_2$H or esters thereof, —CH$_2$NH$_2$ or secondary amines, tertiary amines, quaternary amines or amides thereof, and —CH$_2$OH or esters or ethers thereof; and wherein the furanic compound is optionally bound to a solid support.

6. Method according to claim 1 wherein the dienophile is acetylene, optionally substituted with one or more linear or branched C$_1$-C$_8$ alkyl groups, or wherein the dienophile is a compound according to formula (II)

wherein EWG is an electron withdrawing group and $R_3$=H, linear or branched $C_1$-$C_8$ alkyl.

7. Method according to claim 1, wherein the phenolic compound is one or more phenolic compound selected from the group consisting of compounds according to the following formulae IIIa-IIIh:

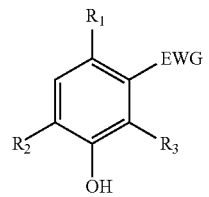
IIIa

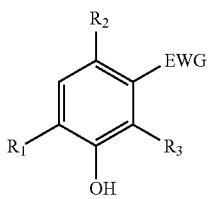
IIIb

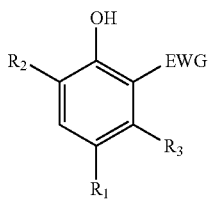
IIIc

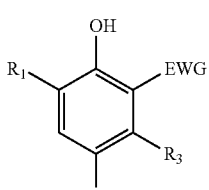
IIId

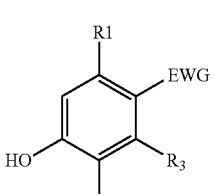
IIIe

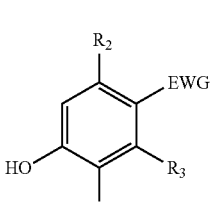
IIIf

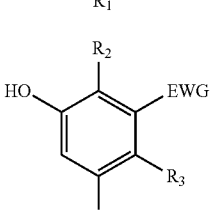
IIIg

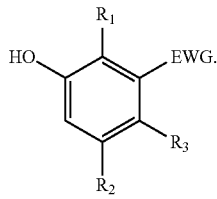
IIIh

8. Method according to claim 1, wherein reacting the furanic compound with the dienophile is carried out in an apolar, aprotic and/or non-coordinating solvent.

9. Method according to claim 1, wherein reacting the furanic compound with the dienophile is carried out at a temperature ranging from −60-350° C.

10. Method according to claim 1, wherein the phenolic compound is reacted further in one or more reaction steps selected from the group consisting of hydrolysis, oxidation, reduction, nucleophilic addition, olefination, rearrangement, decarboxylation, and decarbonylation to obtain a final phenolic product.

11. Method according to claim 10, wherein the final phenolic product is selected from the group consisting of phenol, o-alkylphenol, m-alkylphenol, p-alkylphenol, cresols, o-hydroxybenzoic acid, m-hydroxybenzoic acid, p-hydroxybenzoic acid, 2,6-dialkylphenol, 2,5-dialkylphenol, 2,4-dialkylphenol, 2,3-dialkylphenol, 3,4-dialkylphenol, 3,5-dialkylphenol, xylenols, 2,3,4-trialkylphenol, 2,3,5-trialkylphenol, 2,3,6-trialkylphenol, 2,4,5-trialkylphenol, 2,4,6-trialkylphenol, 3,4,5-trialkylphenol, o-nitrophenol, m-nitrophenol, p-nitrophenol, o-cyanophenol, m-cyanophenol, p-cyanophenol, catechol, resorcinol, hydroquione, o-halophenol, m-halophenol, p-halophenol, o-aminophenol, m-aminophenol, p-aminophenol, o-hydroxystyrene, m-hydroxystyrene, p-hydroxystyrene, o-hydroxybenzyl alcohol, m-hydroxybenzyl alcohol, p-hydroxybenzyl alcohol, o-hydroxybenzyl amine, m-hydroxybenzyl amine, p-hydroxybenzyl amine, o-hydroxyacetophenone, m-hydroxyacetophenone, p-hydroxyacetophenone, o-hydroxybenzaldehyde, m-hydroxybenzaldehyde, p-hydroxybenzaldehyde, o-hydroxybenzamide, m-hydroxybenzamide, p-hydroxybenzamide and combinations thereof.

12. Method according to claim 2, wherein the ligand is a sulfonate ligand.

13. Method according to claim 12, wherein the sulfonate ligand comprises an alkyl group, an aryl group, or an electron-withdrawing group.

14. Method according to claim 13, wherein the electron-withdrawing group is a halogenated group comprising at least one halogen atom, a perhalogenated group, a perfluoroalkyl, or a trifluoromethyl group.

15. Method according to claim 4, wherein the solid support comprises a polymeric support, silica, alumina, silica-alumina, or a zeolite.

16. Method according to claim 6, wherein EWG is I, —CN, —NO$_2$, —CO$_2$X, —C(O)NX, —C(=NY)X, CF$_3$, CCl$_3$, CBr$_3$, CI$_3$, —SO$_2$X, —SO$_3$X, —COH, —COX, —COF, —COCl, —COBr, or —COI, wherein X and Y are independently H, or linear or branched $C_1$-$C_8$ alkyl, optionally substituted with halogens and optionally polymer-supported.

17. Method according to claim 8, wherein the solvent is a $C_4$-$C_{12}$ hydrocarbon, ether, esters, toluene, heptane, or mesitylene.

18. Method according to claim 9, wherein the temperature ranges from 20-180° C.

\* \* \* \* \*